(12) United States Patent
Lampe et al.

(10) Patent No.: US 9,550,731 B2
(45) Date of Patent: Jan. 24, 2017

(54) METHOD FOR PHASE TRANSFER SYNTHESIS OF ORGANIC PEROXIDES

(71) Applicant: Honeywell Federal Manufacturing & Technologies, LLC, Kansas City, MO (US)

(72) Inventors: Matt Lampe, Kansas City, MO (US); Thomas Robison, Kansas City, MO (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 0 days.

(21) Appl. No.: 14/719,364

(22) Filed: May 22, 2015

(65) Prior Publication Data

US 2015/0336886 A1 Nov. 26, 2015

Related U.S. Application Data

(60) Provisional application No. 62/002,004, filed on May 22, 2014.

(51) Int. Cl.
*C07C 409/38* (2006.01)
*C07C 407/00* (2006.01)

(52) U.S. Cl.
CPC ........... *C07C 409/38* (2013.01); *C07C 407/00* (2013.01)

(58) Field of Classification Search
CPC ... C07C 409/38; C07C 407/00; B01J 19/0093; B01J 19/248; B01J 2219/0086; B01J 2219/2401; B01J 2219/2402; B01J 2219/2419; B01J 2219/2444; B01J 2219/2445; B01J 2219/2446; B01J 2219/00781

USPC ........ 558/263, 264; 568/558, 566, 567, 568, 568/578; 560/302
See application file for complete search history.

(56) References Cited

U.S. PATENT DOCUMENTS

| 5,962,746 | A | 10/1999 | Diffendall et al. |
| 7,968,753 | B2 | 6/2011 | Azzawi et al. |
| 2004/0082804 | A1* | 4/2004 | Brophy ............... B01J 19/0093 560/1 |
| 2009/0182162 | A1* | 7/2009 | Corpart ............... C07C 409/04 558/264 |

FOREIGN PATENT DOCUMENTS

| EP | 2010484 | 9/2012 |
| JP | 4940598 B2 | 5/2012 |

OTHER PUBLICATIONS

Baj ("Synthesis of dialkyl peroxides in the presence of polymer-supported phase-transfer catalysts" Applied Catalysis A: General 309, 2006, p. 85-90).*
Phenomenex (Solvent Miscibility Table, 1 p. downloaded from http://gen-lab.hu/dokumentumok/solv_misc.pdf on Apr. 27, 2016).*

* cited by examiner

*Primary Examiner* — Jafar Parsa
*Assistant Examiner* — Amy C Bonaparte
(74) *Attorney, Agent, or Firm* — Hovey Williams LLP

(57) ABSTRACT

Processes and systems for synthesizing organic peroxides are provided. One or more of the reactions described herein may be performed in a continuous reactor, optionally including at least one microscale reaction channel. Additionally, at least one phase transfer catalyst may be used to facilitate reaction of components present in a multiphase reaction mixture.

21 Claims, 1 Drawing Sheet

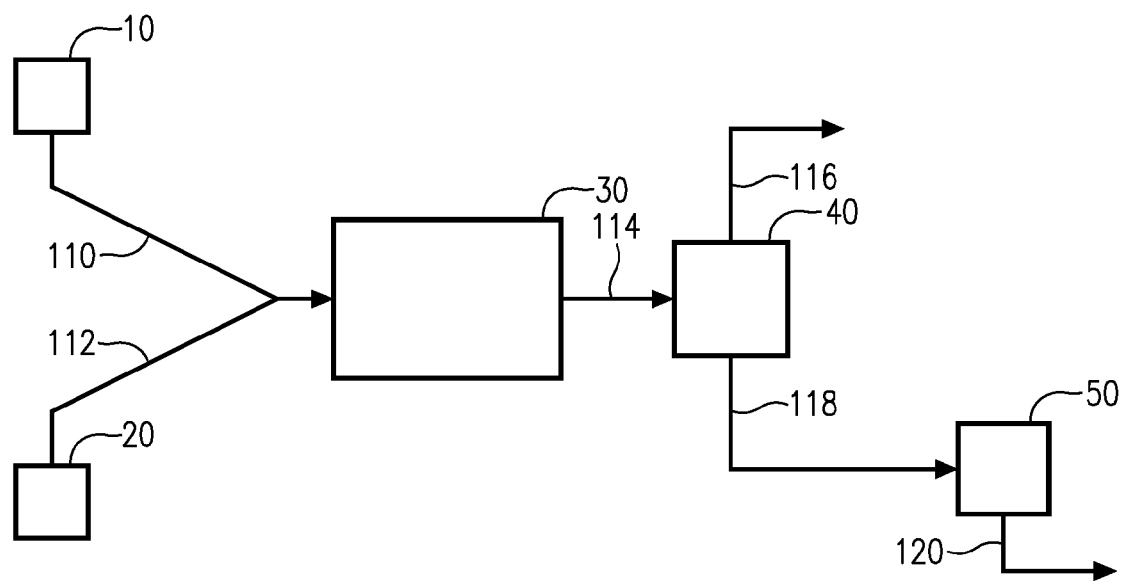

METHOD FOR PHASE TRANSFER SYNTHESIS OF ORGANIC PEROXIDES

CROSS-REFERENCE TO RELATED APPLICATIONS

This application claims priority to U.S. Provisional Patent Application No. 62/002,004, filed on May 22, 2014, the entire disclosure of which is incorporated herein by reference.

BACKGROUND

1. Field

One or more embodiments of the present invention relates to the synthesis of organic compounds. In some aspects, the present invention may related to a phase transfer synthesis of organic peroxides.

2. Description of Related Art

Organic peroxides are a useful class of specialty chemicals employed in a variety of different applications, including, for example, as initiators or promoters in polymerization reactions or in other synthesis reactions for producing organic compounds. However, the reactive nature that makes these materials useful for such applications also presents a unique challenge during their production. In particular, in addition to being highly reactive, organic peroxides have fast, highly exothermic reaction rates and, consequently, must be produced under carefully controlled reaction conditions. Typically, organic peroxides are produced using batch synthesis methods, which are often carried out with large volumes of solvent in order to moderate reaction temperature to reduce the risk of thermal runaway. Continuous processes for synthesizing organic peroxides have also been proposed, but these often require intensive mixing and complex temperature control schemes. Thus, improvement is needed to provide a safe, continuous, and economical process for synthesizing organic peroxides, especially on a commercial scale.

SUMMARY

One embodiment of the present invention concerns a process for synthesizing an organic peroxide. The process comprises reacting an organic hydroperoxide with at least one organic reactant in a multiphase reaction mixture to thereby form an organic peroxide. The multiphase reaction mixture comprises a first reaction phase and a second reaction phase at least partially immiscible in the first reaction phase, wherein the organic hydroperoxide is more miscible in one of the first and second reaction phases than in the other. The multiphase reaction mixture further comprises at least one catalyst for facilitating mass transfer between the first and the second reaction phases. The reacting is carried out in a reaction zone comprising one or more reaction channels and at least one of the reaction channels has one or more of the following characteristics: (i) a total channel volume of less than 75 mL; (ii) a length-to-width ratio of at least 20:1; and/or (iii) an average channel cross-sectional area of less than 10 mm$^2$.

Another embodiment of the present invention concerns a process for synthesizing an organic peroxide. The process comprises providing a first reactant mixture comprising at least one organic reactant selected from the group consisting of alcohols, ketones, acids, esters, ethers, or halides or anhydrides thereof and providing a second reactant mixture comprising at least one pH modifying agent. The first and the second reactant mixtures are at least partially immiscible with one another and at least one of the first and second reactant mixtures include at least one organic hydroperoxide. The process comprises reacting at least a portion of the organic reactant with the organic hydroperoxide in a reaction zone in the presence of at least one phase transfer catalyst to provide the organic peroxide, wherein the reaction zone is at least partially defined within at least one continuous microscale reactor.

Yet another embodiment of the present invention concerns a process for synthesizing an organic peroxide. The process comprises reacting an organic hydroperoxide, or precursor thereto, with at least one organic reactant in multiphase reaction mixture to thereby form an organic peroxide; and recovering at least a portion of the organic peroxide from the reaction mixture. The multiphase reaction mixture comprises a first reaction phase and a second reaction phase at least partially immiscible in the first reaction phase. The organic hydroperoxide is more miscible in one of the first and second reaction phases than in the other. The multiphase reaction mixture further comprises at least one catalyst for facilitating mass transfer between the first and the second reaction phases. Each of the reacting and the recovering is performed in a continuous manner.

BRIEF DESCRIPTION OF THE DRAWINGS

Various embodiments of the present invention are described in detail below with reference to the attached drawing FIGURE, wherein:

FIG. 1 is a schematic depiction of the major steps of a process for synthesizing an organic peroxide according to embodiments of the present invention.

DETAILED DESCRIPTION

The following detailed description of embodiments of the invention is intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the present invention is defined only by claims presented in subsequent regular utility applications, along with the full scope of equivalents to which such claims are entitled.

In this description, references to "one embodiment," "an embodiment," or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, step, etc. described in one embodiment may also be included in other embodiments, but is not necessarily included. Thus, the present technology can include a variety of combinations and/or integrations of the embodiments described herein.

For the purposes of this specification, unless otherwise indicated, all numbers expressing quantities of ingredients, goods, properties, and other parameters used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

All numerical ranges herein include all numerical values and ranges of all numerical values within the recited numerical ranges. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The present invention relates to methods for producing organic compounds and, in particular, to methods for continuously producing organic peroxides and organic hydroperoxides using a multiphase synthesis reaction. Examples of organic peroxides that can be synthesized according to embodiments of the present invention include, but are not limited to, alkyl hydroperoxides having the general formula R—O—O—H, dialkyl peroxides having the general formula R—O—O—R', peroxycarboxylic acids having the general formula R—C(O)—O—O—H, peroxycarboxylic esters having the general formula R—C(O)—O—O—R', diacyl peroxides having the general formula R—C(O)—O—O—C(O)—R', peroxycarbonate esters having the general formula R—O—C(O)—O—O—C(O)—R', peroxydicarbonates having the general formula R—O—C(O)—O—O—C(O)—O—R', ketone peroxides, and perketals, wherein R and R' can be any suitable substituent, including organic substituents. Specific examples of organic peroxides synthesized according to methods of the present invention include, but are not limited to, di-tert-butyl peroxide, di(2-tert-butylperoxyisopropyl)benzene, dicumyl peroxide, peroxyacetic acid, tert-butyl peroxypivalate, tert-butyl peroxy-2-ethylhexanoate, t-butyl-peroxy-2-methylbenzoate, dibenzoyl peroxide, di(3,5,5-trimethylhexanoyl) peroxide, tert-butyl peroxyisopropylcarbonate, tert-butyl peroxy-2-ethylhexylcarbonate, di(4-tert-butylcyclohexyl) peroxydicarbonate, di(2-ethylhexyl) peroxydicarbonate or dicetyl peroxydicarbonate, cyclohexanone peroxide, methyl isobutyl ketone peroxide or methyl ethyl ketone peroxide, 2,2-bis(tert-butylperoxy)butane, 1,1-di-tert-butylperoxy-3,3,5-trimethylcyclohexane, t-butyl-peroxy-2-methyl benzoic acid peroxide, or 1,1-bis(tert-butylperoxy)cyclohexane.

Turning now to FIG. 1, the major steps of a process for synthesizing an organic peroxide according to embodiments of the present invention are schematically depicted. As shown in FIG. 1, a first reactant mixture in line 110 originating from vessel 10 and a second reactant mixture in line 112 originating from vessel 20 can be combined and introduced into a reaction zone 30. In one embodiment of the present invention, the first and second reactant mixtures may be at least partially, or nearly completely, immiscible in each other, so that the reaction carried out in reaction zone 30 may be a multiphase reaction. As shown in FIG. 1, the two-phase product stream in line 114 withdrawn from reaction zone 30 can be separated into a product stream and at least one waste stream in a product separation zone 40. The resulting product stream in line 118 can be subjected to further workup in a downstream product recovery zone 50 and the waste stream in line 116 may be routed to further processing and/or disposal (not shown).

According to one embodiment, the first reactant mixture in vessel 10 may be an organic reactant mixture. When the first reactant mixture is an organic mixture, it may include at least one organic reactant, optionally combined with at least one solvent. Depending in part on the final organic peroxide product being synthesized, the organic reactant can include, for example, one or more alcohols, ketones, acids, esters, ethers, halides or anhydrides of one or more of these compounds. These organic reactants can include one or more aromatic compounds, one or more aliphatic compounds, or one or more alicyclic compounds, depending on the final peroxide product being synthesized. Exemplary organic reactants can include, but are not limited to, acyl halides such as o-toluoyl chloride and benzoyl chloride. In one embodiment, mixtures of two or more organic reactants can be employed in the first reactant phase, optionally combined with one or more solvents.

When present, the solvent can comprise an organic solvent that is substantially miscible with the organic reactant. Examples of suitable solvents can include, but are not limited to, mineral spirits and hexane. The solvent can be present in any suitable amount and, in one embodiment, can be present such that the weight ratio of solvent to organic reactant is at least about 0.05:1, at least about 0.10:1, or at least about 0.25:1 and/or not more than about 1:1, not more than about 0.75:1, or not more than about 0.50:1. In one embodiment, substantially no solvent is used and the first reactant mixture may consist, or consist essentially of, one or more organic reactants as described above. In some embodiments, an excess of solvent may be used, such that the weight ratio of solvent to organic reactant is at least about 1.5:1, at least about 2:1, at least about 4:1, at least about 5:1 and/or not more than about 50:1, not more than about 30:1, not more than about 20:1, not more than about 10:1, not more than about 6:1.

According to one embodiment, the second reactant mixture can be a reactant mixture that is at least partially immiscible with the first reactant mixture. In some embodiments, the second reactant mixture can be an aqueous reactant mixture, while, in other embodiments, the second reactant mixture may be another organic reactant mixture having limited or no miscibility with the first reactant mixture. In one embodiment, the second reactant mixture can include at least one organic hydroperoxide and at least one pH modifying agent at least partially dissolved in at least one solvent. When the second reactant mixture is an aqueous reactant mixture, the solvent may comprise or be water.

The weight ratio of organic hydroperoxide to the pH modifying agent in the second reactant mixture can be at least about 0.25:1, at least about 0.5:1, at least about 0.75:1, or at least about 1:1 and/or not more than about 10:1, not more than about 5:1, not more than about 3:1, or not more than about 2:1. The organic hydroperoxide can be present in the second reactant mixture in an amount of at least about 0.25 weight percent, at least about 0.5, at least about 1, at least about 5, at least about 10, or at least about 25 weight percent and/or not more than 75 weight percent, not more than about 50 weight percent, not more than about 25 weight percent, or not more than about 10 weight percent, based on the total weight of the second reactant mixture, but the concentration may vary depending on the final product and specific reaction conditions. In some embodiments, the organic hydroperoxide can be present in the second reactant mixture in an amount of at least about 85, at least about 90, at least about 95 percent, or the second reactant mixture can consist essentially of, or consist of, organic hydroperoxide. Any suitable organic hydroperoxide may be used, and may depend, for example, on the final product being synthesized. In one embodiment, the organic hydroperoxide can be hydrogen peroxide, while, in other embodiments, organic hydroperoxides such as, for example, t-butyl hydroperoxide can be used, although other organic hydroperoxides may also be employed within the scope of the present invention.

Depending on the specific synthesis being performed, the pH modifying agent can be an acid or a base. In one embodiment, when the organic reactant includes, for example, organic anhydrides or carboxylic acids, the pH modifying agent can comprise an acid. Suitable acids can include, for example, sulfuric acid, acetic acid, and hydrochloric acid, although others could also be used. In other embodiments, the pH modifying agent may be a base. Suitable bases can include, for example, hydroxides, carbonates, and bicarbonates of potassium, calcium, or sodium, although others could be used. In addition, at least one of the first and second reaction phases may also comprise one or more other catalysts or additives such as emulsifiers and phlegmatizing agents, which can include, for example, isododecane, white oil, and phthalates. In some embodiments, one or more salts, including, for example, cuprous chloride, or cobalt or magnesium salts, may also be present in one of the reaction phases, such as, for example, the aqueous phase, optionally with ammonia or other basic compound.

Additionally, the synthesis reaction performed in reaction zone 30 may be carried out in the presence of at least one phase transfer catalyst (PTC). As used herein, the term "phase transfer catalyst" refers to a component that facilitates mass transfer between phases of a multi-phase mixture. The PTC employed in embodiments of the present invention may be introduced into reaction zone 30 with the first and/or second reactant mixtures in lines 110 and/or 112, or may be introduced into reaction zone 30 via a separate line (embodiment not shown). Other methods of introduction may also be used. The molar ratio of PTC to the organic hydroperoxide in the combined reaction mixture can be at least about 1:50, at least about 1:20, at least about 1:15, or at least about 1:12 and/or not more than about 2:1, not more than about 1:4, not more than about 1:8, or not more than about 1:10. Suitable PTCs can include, but are not limited to, quaternary ammonium salts, such as tetraalkylammonium and tetraalkylphosphonium salts, and crown ethers. Tetrabutylammonium bisulfate is one example of a PTC suitable for use in embodiments of the present invention.

Alternatively, in some embodiments, the organic hydroperoxide described above may be less soluble in one of the reactant phases and may be combined with the reactant mixture with which it is most miscible. In some embodiments, the organic hydroperoxide may have low or no solubility in the aqueous or other organic phase and may be combined with the organic reactant and optional solvent, rather than be present in the second reactant mixture as described above. In this case, the second reactant mixture, which can be an aqueous or another organic mixture, could include at least one pH modifying agent and a PTC, optionally combined with one or more optional additives as described previously.

Turning again to FIG. 1, the stream of a second reactant mixture in line 112 discharged from vessel 20 can be combined with a stream of a first reactant mixture withdrawn from vessel 10 via line 110 and the combined stream may be passed into reaction zone 30. Although shown in FIG. 1 as being combined prior to introduction into reaction zone 30, it is also possible that the two reactant mixtures may be combined within reaction zone 30 (not shown). Additionally, in some embodiments, one or more of the reaction components may be introduced into reaction zone 30 via at least one additional stream (not shown) other than the streams in lines 110 and line 112 depicted in FIG. 1. The additional reactant streams, when present, can comprise aqueous or organic phases and may include at least one of the reactants, solvents, and/or additives discussed above. Additionally, the additional reactant streams may be combined with one or more other reactant streams in or prior reaction zone 30, as discussed previously.

Prior to entering reaction zone 30, each of the reactant streams, including the streams in lines 110 and 112 of FIG. 1, may be pressurized via separate pumps (not shown) prior to being combined in or adjacent reaction zone 30. Suitable pumps can include, for example, volumetric or pressure-driven pumps or peristaltic pumps, although other types of pumps may be used as well. Typically, the average reaction pressure of the reaction mixture passing through reaction zone 30 can be at least about 1 bar, at least about 2 bar, or at least about 4 bar, at least about 10 bar, at least about 20 bar, at least about 50 bar, at least about 100 bar and/or not more than about 500 bar, not more than about 250 bar, not more than about 100 bar, not more than about 75 bar, not more than about 50 bar, not more than about 20 bar, not more than about 15 bar, or not more than about 12 bar.

As the combined reaction mixture passes through reaction zone 30, the reagents present in reaction zone 30 react to form the organic peroxide product. In one embodiment, reaction zone 30 may be equipped with a temperature control system (not shown in FIG. 1) configured to monitor reaction temperature and to remove or add heat from the reaction zone 30 as needed. In some embodiments, the temperature control system may comprise a cooling system configured to remove heat from the reaction mixture in order to avoid hot spots. According to one embodiment, the average temperature of the reaction mixture passing through reaction zone 30 can be less than about 40° C., less than about 35° C., less than about 30° C., less than about 27° C., less than about 20° C., less than about 15° C., less than about 10° C., less than about 5° C., less than 0° C.

In another embodiment, the temperature control system may comprise a heating system configured to supply heat to the reaction mixture passing through reaction zone 30. When reaction zone 30 includes a heating system, the average temperature of the reaction mixture passing through reaction zone 30 may be at least about 40° C., at least about 50° C., at least about 75° C., at least about 90° C., or at least about 100° C. In some embodiments, the temperature control system may comprise both a heating and a cooling system configured to add or remove heat from the reaction medium in reaction zone 30 as needed in order to maintain the average reaction temperature within one or more temperature ranges specified above.

The temperature control system employed in reaction zone 30 can include one or more thermocouples or other temperature indicating devices for detecting and monitoring the temperature of the reaction medium passing through reaction zone 30. Additionally, in one embodiment, the temperature control system may include a heat transfer medium for transferring heat to and from the reaction medium. In one embodiment, the heat transfer medium can be a liquid passing in indirect heat exchange relationship with the reaction medium in at least one reaction channel. When the heat exchange medium comprises a liquid, it can include any suitable type of liquid such as, for example, synthetic heat transfer fluids, brine, a water/alcohol mixture, or water. In some embodiments, the reaction channels may be configured so that air or other vapor-phase medium can be passed between the channels and used as a heat transfer medium.

In some embodiments, the heat transfer medium can comprise a solid heat exchange material in thermal contact with at least a portion of the reaction medium in reaction zone 30, which is heated or cooled to provide heat to or remove heat from reaction zone 30. Examples of suitable solid heat exchange materials can include, but are not limited to, strips or pieces of metal or other conductive material disposed within or proximate to one or more of the reaction channels that are in thermal contact with at least a portion of the reaction medium passing therethrough. Optionally, one or more components of the temperature control system can be in communication with one another via computer or other device, such that the control system can operate automatically to sense and control the reaction temperature within a desired range.

In some embodiments, the reaction mixture may pass through reaction zone 30 in a laminar flow regime (i.e., Reynolds number less than 2,000), while in other embodiments, the reaction mixture passing through reaction zone 30 may do so in a non-laminar (i.e., Reynolds number>2,000) manner. In one embodiment, the Reynolds number of the reaction medium flowing through reaction zone 30 can be at least about 2,500, at least about 5,000, or at least about 7,500. Although the flow rate of the reactants may vary, depending on the specific reactor configuration, the average residence time of the reaction mixture in reaction zone 30 can be less than about 5 minutes, less than about 2 minutes, less than about 1 minute, or less than about 30 seconds. The ratio of the flow rate of the first reactant stream in conduit 110 to the second reactant stream in conduit 112 can be at least about 0.05:1, at least about 0.10:1, at least about 0.15:1, at least about 0.25:1, or at least about 0.50:1 and/or not more than about 1.5:1, not more than about 1:1, or not more than about 0.75:1, although other ratios may also be suitable depending on the specific reaction being carried out.

Structurally, reaction zone 30 can include at least one continuous reactor for receiving and facilitating reaction between the reactant mixtures. In one embodiment, the reactor can be a micro-scale reactor and can include at least one micro-scale reaction channel through which the combined reaction mixture flows. As used herein, the prefix "micro-," as applied to various types of process equipment, including reactors and reaction channels, refers to equipment having dimensions that are on a millimeter scale, although, in one embodiment, micro-reactors, microchannels, and other micro-equipment may also have at least one dimension on a micron scale. The micro-reactors used some embodiments of the present invention can include a single micro-scale reaction channel, while, in other embodiments, the reactor can include at least 2, at least 5, at least 10, at least 25, at least 50, or 100 or more channels.

Although the specific dimensions of each individual reaction channel may vary depending on the exact configuration of the micro-reactor used in reaction zone 30, the total volume of a single micro-scale reaction channel, according to one embodiment, can be not more than about 75 mL, not more than about 50 mL, not more than about 25 mL, not more than about 20 mL, not more than about 16 mL, not more than about 10 mL, not more than about 5 mL, not more than about 2 mL, not more than about 1 mL, or not more than about 0.5 mL, with the total reactor volume increasing with an increased number of microchannels. The ratio of the length, or longest dimension, of a single flow channel to its width, or second longest dimension, may be at least about 20:1, at least about 50:1, or at least about 75:1 and/or not more than about 50,000:1, not more than about 25,000:1, not more than about 10,000:1, not more than about 5000:1, not more than about 2500:1, not more than about 1000:1, not more than about 500:1, not more than about 250:1, or not more than about 100:1.

Each channel can have any suitable shape and may, for example, have a cross-sectional shape that is substantially square, rectangular, circular, elliptical, or semi-circular. In one embodiment, regardless of shape, the average cross-sectional area of each channel can be at least about 0.001, at least about 0.005, at least about 0.01, at least about 0.05, or at least about 0.10 square millimeters ($mm^2$) and/or not more than about 10, not more than about 7, or not more than about 5 $mm^2$. The shape and area of the cross-section may remain substantially constant along the length of each channel and/or amongst several channels where multiple channels are employed in a single reactor.

Although the specific geometry and relative configuration of the reaction channels is also not necessarily limited, in one embodiment, the micro-channels utilized in the present invention can have significantly simpler geometries, as compared to, for example, conventional micro-scale reaction devices that include tortuous flow paths and multiple internal mixing devices. For example, in one embodiment, the reaction channels can comprise one or more lengths of small diameter tubing. In some embodiments, the micro-reactor utilized in reaction zone 30 of the present invention can include one or more substantially straight reaction micro-channels that include no more than 5, no more than 4, no more than 3, no more than 2, or no more than 1 turn or bend having an angle greater than 30° and/or may include no turns or bends having an angle greater than 60°, greater than 75°, or greater than 80°. Additionally, in one embodiment, the micro-scale flow channel can have an average tortuosity factor of less than about 1.5, less than about 1.2, or less than about 1.1, wherein the average tortuosity factor is defined as the ratio of the length of total flow path of a reaction channel defined between the channel inlet and channel outlet to the length of straight line drawn directly between the center point of the channel inlet and the center point of the channel outlet.

In one embodiment of the present invention, the reaction performed in reaction zone 30 can be carried out with substantially no mixing of the reactant phases, other than the mixing that occurs when the two phases are combined to initiate the reaction. For example, reaction zone 30 can be free of mechanical mixers and agitators and may also include no static mixers. In one embodiment, the reaction mixture may be divided and recombined no more than 3 times, no more than 2 times, or no more than 1 time within reaction zone 30, or may not be divided and recombined at all within reaction zone 30. Additionally, according to embodiments of the present invention, the reaction mixture may receive substantially no mechanical energy from external sources as it passes through reaction zone 30.

When multiple reaction channels are utilized, the channels may be arranged on a single plane, and the reactor may be configured to include, for example, multiple parallel channels cut into a single glass wafer, or a plurality of small-diameter tubes arranged in a generally side-by-side configuration. In one embodiment, multiple wafers, each having a plurality of channels cut into at least one surface, may also be stacked vertically to create a stacked wafer configuration, which can provide additional reaction volume for larger-scale operations. Additionally, one or more meso-reactors, optionally oscillatory flow meso-reactors, may also be used. The reactors may be constructed from any suitable material, as long as the materials are inert to the reaction phases passing therethrough. Examples of suitable materials include, but are not limited to, glass or polymeric materials, including various fluoropolymers. In one embodiment, at least a portion of one or more reaction channels may optionally include at least one reactive solid, such as a solid catalyst, at least partially filling a portion of the reaction channel. In some embodiments, at least a portion of the interior wall of the reaction channel can be lined with, or formed from, a solid catalyst or absorbent material.

Referring again to FIG. 1, the two-phase organic peroxide-containing product stream exiting reaction zone 30 via line 114 can be passed to a product separation zone 40, wherein the two phases are separated. Product separation zone 40 can include any suitable type of system configured to separate the crude product stream in line 114 into a separated product stream in line 118 and a waste stream in line 116. Examples of separation systems suitable for use in product separation zone 40 can include, but are not limited to, a membrane separator, a decanter, or a liquid-liquid extractor. The waste stream withdrawn from product separation zone 40 via line 116 can be routed for subsequent processing and/or disposal (not shown), while the product stream exiting product separation zone 40 via line 118 can be routed to a product recovery zone 50, wherein the final peroxide product is further processed and recovered. Examples of processes used to recover the final peroxide product can include, but are not limited to, one or more washings, such as, for example, water washings, of the product phase to remove impurities and/or passage through one or more drying beds packed with desiccant. Other purification or recovery processes may also be used before recovering the final organic peroxide product in line 120.

In one embodiment, the actual yield of the organic peroxide in line 120 can be at least about 50, at least about 60, at least about 70, at least about 75, at least about 80, at least about 85, at least about 90 percent. Once recovered in product recovery zone 50 as shown in FIG. 1, the final organic peroxide product may be routed via line 120 for further processing, storage, and/or use.

The following example is intended to be illustrative of the present invention in order to teach one of ordinary skill in the art to make and use the invention and are not intended to limit the scope of the invention in any way.

EXAMPLE

A first reactant solution (Solution A) was prepared by dissolving 28 grams of tetrabutylammonium bisulfate, 111 mL of tert-butyl hydroperoxide, and 99 grams of sodium hydroxide pellets in deionized water. The total volume of the solution was 687 mL. A second reactant solution (Solution B) was prepared by dissolving 100 grams of o-toluoyl chloride in 34 grams of mineral spirits. Solution A was allowed to cool to room temperature.

A stream of Solution A and a stream of Solution B were simultaneously introduced into a microscale reaction channel defined by a length of 0.5-mm ID tubing having a total volume of 4 mL. The streams were introduced into the tubing with an Asia microfluidics dual pump system available from Syrris, Inc. The flow rate of the stream of Solution A was 2.5 mL/min and the volumetric flow rate of the stream of Solution B was 0.454 mL/min. The product stream collected from the reaction channel was phase separated and dried over magnesium sulfate. The yield of tert-butyl 2-methylperbenzoate in mineral spirits was approximately 95 grams, or 75 weigh percent. The active oxygen content of the peroxide was 5.9%.

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

The invention claimed is:

1. A process for synthesizing an organic peroxide, said process comprising:
    reacting an organic hydroperoxide with at least one organic reactant in a multiphase reaction mixture to thereby form an organic peroxide,
    wherein said multiphase reaction mixture comprises a first reaction phase and a second reaction phase at least partially immiscible in said first reaction phase, wherein said organic hydroperoxide is more miscible in one of said first and second reaction phases than in the other,
    wherein said multiphase reaction mixture further comprises at least one catalyst for facilitating mass transfer between said first and said second reaction phases,
    wherein said reacting is carried out in a reaction zone comprising at least two reaction channels, wherein each of said reaction channels includes no turns or bends having an angle greater than 80°, wherein said reaction channels are arranged in a parallel configuration and each of said reaction channels has one or more of the following characteristics (i) through (iii)—
        (i) a total channel volume of less than 75 mL;
        (ii) a length-to-width ratio of at least 20:1; and/or
        (iii) an average channel cross-sectional area of less than 10 mm$^2$.

2. The process of claim 1, wherein said organic reactant is more miscible in said first reaction phase and said organic hydroperoxide is more miscible in said second reaction phase, wherein said second reaction phase is an aqueous reaction phase.

3. The process of claim 2, wherein at least one of said first and said second reaction phases further comprises at least one pH modifying agent.

4. The process of claim 1, wherein said organic reactant comprises an organic halide.

5. The process of claim 1, wherein said reacting includes heating said multiphase reaction mixture to a temperature of at least 40° C.

6. The process of claim 1, wherein said reacting includes cooling said multiphase reaction mixture to a temperature of less than 40° C.

7. The process of claim 1, wherein said reacting comprises passing said multiphase reaction mixture through said reaction channel, wherein the Reynolds Number of the reaction mixture passing through said reaction channel is greater than 5,000.

8. The process of claim 1, wherein said reaction zone comprises at least 5 reaction channels.

9. The process of claim 8, wherein each of said reaction channels comprises a substantially straight reaction channel, wherein none of said reaction channels includes any bends or turns having an angle greater than 80°.

10. The process of claim 1, wherein at least one of said reaction channels is a substantially straight reaction channel having a tortuosity factor of less than 1.5.

11. The process of claim 1, wherein said reaction channels have at least two of characteristics (i) through (iii).

12. The process of claim 1, wherein said reaction channels have all three of characteristics (i) through (iii).

13. A process for synthesizing an organic peroxide, said process comprising:
   (a) providing a first reactant mixture comprising at least one organic reactant selected from the group consisting of alcohols, ketones, acids, esters, ethers, or halides or anhydrides thereof;
   (b) providing a second reactant mixture comprising at least one pH modifying agent, wherein said first and said second reactant mixtures are at least partially immiscible with one another, and wherein at least one of said first and second reactant mixtures include at least one organic hydroperoxide;
   (c) reacting at least a portion of said organic reactant with said organic hydroperoxide in a reaction zone in the presence of at least one phase transfer catalyst to thereby provide said organic peroxide,
   wherein said reaction zone is at least partially defined within at least one continuous microscale reactor, wherein said microscale reactor includes at least two reaction channels, wherein each of said reaction channels includes no turns or bends having an angle greater than 80°, and wherein said reaction channels are arranged in a parallel configuration.

14. The process of claim 13, wherein said second reactant mixture comprises said organic hydroperoxide and water.

15. The process of claim 13, wherein said pH modifying agent is a base.

16. The process of claim 13, further comprising combining said first reactant mixture and said second reactant mixture to form a combined reactant mixture and reacting said combined reactant mixture during said reacting of step (c).

17. The process of claim 13, wherein each of said channels is a substantially straight channel having a tortuosity factor of less than 1.5:1.

18. A process for synthesizing an organic peroxide, said process comprising:
   (a) reacting an organic hydroperoxide with at least one organic reactant in a multiphase reaction mixture in a reaction zone to thereby form an organic peroxide, wherein the average residence time of said reaction mixture in said reaction zone is less than 5 minutes; and
   (b) recovering at least a portion of said organic peroxide from at least a portion of said reaction mixture,
   wherein said multiphase reaction mixture comprises a first reaction phase and a second reaction phase at least partially immiscible in said first reaction phase, wherein said organic hydroperoxide is more miscible in one of said first and second reaction phases than in the other,
   wherein said multiphase reaction mixture further comprises at least one catalyst for facilitating mass transfer between said first and said second reaction phases, and
   wherein each of said reacting and said recovering is performed in a continuous manner, and wherein said reaction zone comprises at least two substantially straight reaction channels arranged in a parallel configuration, wherein each of said reaction channels includes no turns or bends having an angle greater than 80 degrees, and wherein said organic peroxide comprises t-butyl-peroxy-2-methylbenzoate.

19. The process of claim 18, wherein said first reaction phase is an organic phase comprising said organic reactant and wherein said second reaction phase is an aqueous phase comprising said organic hydroperoxide.

20. The process of claim 19, wherein said multiphase reaction mixture further comprises at least one pH modifying agent.

21. The process of claim 18, wherein said recovering includes separating said multiphase reaction mixture into a product stream and a waste stream; and washing at least a portion of said product stream to provide said organic peroxide.

* * * * *

UNITED STATES PATENT AND TRADEMARK OFFICE
CERTIFICATE OF CORRECTION

PATENT NO.        : 9,550,731 B2
APPLICATION NO.   : 14/719364
DATED             : January 24, 2017
INVENTOR(S)       : Matt Lampe and Thomas Robison Page 1 of 1

It is certified that error appears in the above-identified patent and that said Letters Patent is hereby corrected as shown below:

In the Specification

Column 1, Line 11 add:
-- STATEMENT REGARDING FEDERALLY-SPONSORED RESEARCH OR DEVELOPMENT
This invention was made with government support under Contract No.: DE-NA0000622 awarded by the Department of Energy. The government has certain rights in the invention. --

Signed and Sealed this
Fourteenth Day of April, 2020

Andrei Iancu
*Director of the United States Patent and Trademark Office*